(12) United States Patent
Nørregaard-Madsen et al.

(10) Patent No.: US 6,893,855 B2
(45) Date of Patent: May 17, 2005

(54) SUBTILASE VARIANTS

(75) Inventors: Mads Nørregaard-Madsen, Birkerød (DK); Line Bloch Larsen, Bagsværd (DK); Peter Kamp Hansen, Lejre (DK)

(73) Assignee: Novozymes A/S, Bagsvaerd (DK)

( * ) Notice: Subject to any disclaimer, the term of this patent is extended or adjusted under 35 U.S.C. 154(b) by 282 days.

(21) Appl. No.: 09/976,414

(22) Filed: Oct. 12, 2001

(65) Prior Publication Data

US 2002/0155575 A1 Oct. 24, 2002

Related U.S. Application Data

(60) Provisional application No. 60/241,201, filed on Oct. 17, 2000.

(30) Foreign Application Priority Data

Oct. 13, 2000 (DK) .......................... 2000 01528

(51) Int. Cl.[7] .............................. C12N 9/54; C12N 9/56; C12N 15/57; C12N 15/74; C11D 3/386
(52) U.S. Cl. ...................... 435/220; 435/221; 435/222; 435/69.1; 435/282.3; 435/320.1; 435/471; 536/23.2; 510/350
(58) Field of Search .................... 435/220, 221, 435/222, 69.1, 252.3, 320.1, 471; 510/300, 306; 536/23.2

(56) References Cited

U.S. PATENT DOCUMENTS 6,506,589 B1 * 1/2003 Hastrup et al. ............. 435/221
6,605,458 B1 * 8/2003 Hansen et al. ............. 435/220

FOREIGN PATENT DOCUMENTS

| US | 20030148495 A1 * | 8/2002 | ............. 435/222 |
|---|---|---|---|
| WO | WO 99/27082 | 6/1999 | |
| WO | 01/44452 | 6/2001 | |
| WO | 92/21760 | 3/2002 | |

* cited by examiner

Primary Examiner—Nashaat Nashed
Assistant Examiner—William W. Moore
(74) Attorney, Agent, or Firm—Elias Lambiris

(57) ABSTRACT

The present invention relates to subtilase variants having a reduced tendency towards inhibition by substances present in eggs, such as trypsin inhibitor type IV-0. In particular, the variants comprise at least one additional amino acid residue between positions 42–43, 51–56, 155–161, 187–190, 216–217, 217–218 or 218–219 (in BASBPN numbering). These subtilase variants are useful exhibiting excellent or improved wash performance on egg stains when used in e.g. cleaning or detergent compositions, such as laundry detergent compositions and dishwash composition, including automatic dishwash compositions. Also, isolated DNA sequences encoding the variants, expression vectors, host cells, and methods for producing and using the variants of the invention. Further, cleaning and detergent compositions comprising the variants are disclosed.

32 Claims, 1 Drawing Sheet

```
No:  1         10         20         30         40         50
a)   AQSVPYGVSQIKAPALHSQGYTGSNVKVAVIDSGIDSSHPDLKVAGGASM
b)   AQSVPWGISRVQAPAAHNRGLTGSGVKVAVLDTGI*STHPDLNIRGGASF

No:            60         70         80         90        100
a)   VPSETNPFQDNNSHGTHVAGTVAALNNSIGVLGVAPSASLYAVKVLGADG
b)   VPGEPST*QDGNGHGTHVAGTVAALNNSIGVIGVAPSADLYAVKVLGANG

No:           110        120        130        140        150
a)   SGQYSWIINGIEWAIANNMDVINMSLGGPSGSAALKAAVDKAVASGVVVV
b)   RGSVSGIAQGLEWAAANNMHIANMSLGSDAPSTTLERAVNYATSQGVLVI

No:           160        170        180        190        200
a)   AAAGNEGTSGSSSTVGYPGKYPSVIAVGAVDSSNQRASFSSVGPELDVMA
b)   AATGNNG*SGS***VGYPARYANAMAVGATDQNNRRANFSQYGTGIDIVA

No:           210        220        230        240        250
a)   PGVSIQSTLPGNKYGAYNGTSMASPHVAGAAALILSKHPNWTNTQVRSSL
b)   PGVDIESTYPGSSYDSLSGTSMATPHVAGVAALVKQKNPSWSNVQIRNHL

No:           260        270  275
a)   ENTTTKLGDSFYYGKGLINVQAAAQ
b)   KNTATSLGSTNLYGSGLVNAEAATR
```

```
No:   1         10        20        30        40        50
a)    AQSVPYGVSQIKAPALHSQGYTGSNVKVAVIDSGIDSSHPDLKVAGGASM
b)    AQSVPWGISRVQAPAAHNRGLTGSGVKVAVLDTGI*STHPDLNIRGGASF

No:             60        70        80        90        100
a)    VPSETNPFQDNNSHGTHVAGTVAALNNSIGVLGVAPSASLYAVKVLGADG
b)    VPGEPST*QDGNGHGTHVAGTVAALNNSIGVIGVAPSADLYAVKVLGANG

No:             110       120       130       140       150
a)    SGQYSWIINGIEWAIANNMDVINMSLGGPSGSAALKAAVDKAVASGVVVV
b)    RGSVSGIAQGLEWAAANNMHIANMSLGSDAPSTTLERAVNYATSQGVLVI

No:             160       170       180       190       200
a)    AAAGNEGTSGSSSTVGYPGKYPSVIAVGAVDSSNQRASFSSVGPELDVMA
b)    AATGNNG*SGS***VGYPARYANAMAVGATDQNNRRANFSQYGTGIDIVA

No:             210       220       230       240       250
a)    PGVSIQSTLPGNKYGAYNGTSMASPHVAGAAALILSKHPNWTNTQVRSSL
b)    PGVDIESTYPGSSYDSLSGTSMATPHVAGVAALVKQKNPSWSNVQIRNHL

No:             260       270  275
a)    ENTTTKLGDSFYYGKGLINVQAAAQ
b)    KNTATSLGSTNLYGSGLVNAEAATR
```

Fig. 1

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ala Gly Lys Ala Leu
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Ala Gly Gly Leu
1

<210> SEQ ID NO 3
<211> LENGTH: 40
<212> TYPE: DNA
<213> ORGANISM: Artificial Sequence
<220> FEATURE:
<223> OTHER INFORMATION: Primer

<400> SEQUENCE: 3
ccgaacctga accatccgcg gcccctagga ctttaacagc                40

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gagttaagcc cagaagatgt ggacgcg                27

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
catcgatgta ccgtttggta agctggcata tgttg             35

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
aaccgcacag cgttttttta ttgattaacg cgttgc            36

<210> SEQ ID NO 7
<211> LENGTH: 275
<212> TYPE: PRT
<213> ORGANISM: Bacillus

<400> SEQUENCE: 7

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

-continued

```
Leu Gly Asp Ser Phe Tyr Tyr Gly Lys Gly Leu Ile Asn Val Gln Ala
            260                 265                 270

Ala Ala Gln
        275

<210> SEQ ID NO 8
<211> LENGTH: 269
<212> TYPE: PRT
<213> ORGANISM: Bacillus

<400> SEQUENCE: 8

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

SUBTILASE VARIANTS

CROSS-REFERENCE TO RELATED APPLICATIONS

This application claims, under 35 U.S.C. 119, priority or the benefit of Danish application no. PA 2000 01528 filed Oct. 13, 2000 and U.S. provisional application No. 60/241,201 filed Oct. 17, 2000, the contents of which are fully incorporated herein by reference.

FIELD OF THE INVENTION

The present invention relates to subtilase variants having a reduced tendency towards inhibition by substances present in eggs, such as trypsin inhibitor type IV-0. In particular, the present invention relates to subtilase variants comprising at least one additional amino acid residue between positions 42–43, 51–55, 155–160, 187–189, 217–218 or 218–219 (in subtilisin BPN' (BASBPN) numbering, vide infra). These subtilase variants are useful exhibiting excellent or improved wash performance on egg stains when used in e.g. cleaning or detergent compositions, such as laundry detergent compositions and dishwash composition, including automatic dishwash compositions. The present invention also relates to isolated DNA sequences encoding the variants, expression vectors, host cells, and methods for producing and using the variants of the invention. Further, the present invention relates to cleaning and detergent compositions comprising the variants of the invention.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novozymes A/S), RELASE® (Novozymes A/S), MAXAPEM® PURAFECT® (Genencor International, Inc.).

Further, a number of protease variants are described in the art. A thorough list of prior art protease variants is given in WO 99/27082.

However, even though a number of useful proteases and protease variants have been described, there is still a need for new improved proteases or protease variants for a number of industrial uses.

In particular, the problem of removing egg stains from e.g. laundry or hard surfaces has been pronounced due to the fact that substances present in the egg white inhibit many serine proteases. Examples of such substances include trypsin inhibitor type IV-0 (Ovo-inhibitor) and trypsin inhibitor type III-0 (Ovomucoid).

Therefore, an object of the present invention is to provide improved subtilase enzymes, which are not, or which are only to a limited extent, inhibited by such substances. A further object of the present invention is to provide improved subtilase enzymes that are suitable for removal of egg stains from, for example, laundry and/or hard surfaces.

SUMMARY OF THE INVENTION

Thus, in a first aspect the present invention relates to a subtilase variant selected from the group consisting of (a) a subtilase variant comprising an insertion of at least one additional amino acid residue between positions 42 and 43 (BASBPN numbering);

(b) a subtilase variant comprising an insertion of at least one additional amino acid residue between positions 51 and 56 (BASBPN numbering);

(c) a subtilase variant comprising an insertion of at least one additional amino acid residue between positions 155 and 161 (BASBPN numbering);

(d) a subtilase variant comprising an insertion of at least one additional amino acid residue between positions 187 and 190 (BASBPN numbering);

(e) a subtilase variant comprising an insertion of at least one additional amino acid residue between positions 216 and 217 (BASBPN numbering); and (f) a subtilase variant comprising an insertion of at least one additional amino acid residue between positions 217 and 218 (BASBPN numbering); and (g) a subtilase variant comprising an insertion of at least one additional amino acid residue between positions 218 and 219 (BASBPN numbering).

In a second aspect the present invention relates to an isolated nucleic acid sequence comprising a nucleic acid sequence that encodes for a subtilase variant according to the invention.

In a third aspect the present invention relates to a nucleic acid construct comprising the nucleic acid sequence according to the invention operably linked to one or more control sequences capable of directing the expression of the subtilase in a suitable host.

In a fourth aspect the present invention relates to a recombinant expression vector comprising the nucleic acid construct according to the invention, a promoter, and transcriptional and translational stop signals.

In a fifth aspect the present invention relates to a recombinant host cell comprising the nucleic acid construct of the invention.

In a sixth aspect the present invention relates to a method for producing a subtilase variant according to the invention, the method comprising:

(a) cultivating a recombinant host cell according to the invention under conditions conducive to the production of the subtilase; and (b) recovering the subtilase variant.

In a seventh aspect the present invention relates to a method for producing a subtilase variant according to the invention, the method comprising:

(a) cultivating a strain from the genus Bacillus, preferably from the species *Bacillus clausii*, such as *Bacillus clausii* DSM 13585, to produce a supernatant comprising the subtilase variant; and (b) recovering the subtilase variant.

In an eight aspect the present invention relates to a cleaning or detergent composition, preferably a laundry or dishwash composition, comprising a subtilase variant according to the invention.

Further aspects of the present invention relate to use of the subtilases according to the invention in a cleaning or detergent composition; use of the subtilases or the compositions according to the invention for removal of egg stains; a method for cleaning or washing, including a method for removal of egg stains from, a hard surface or laundry comprising contacting the hard surface or the laundry with the composition of the invention.

In a seventh aspect the present invention relates to a method for removal of egg stains from a hard surface or from laundry, the method comprising contacting the egg stain-containing hard surface or the egg stain-containing laundry with a cleaning or detergent composition, preferably a laundry or dishwash composition, which contains a subtilase variant according to the invention.

Concerning alignment and numbering reference is made to FIG. 1 which shows an alignments between subtilisin BPN' (a) (BASBPN) (SEQ ID NO: 7) and subtilisin 309 (b) (BLSAVI) (SEQ ID NO: 8).

These alignments are in this patent application used as a reference for numbering the residues.

DEFINITIONS

Prior to discussing this invention in further detail, the following terms and conventions will first be defined.
Nomenclature of Amino Acids and Nucleic Acids Throughout the specification, figures and claims the recognized IUPAC nomenclature for amino acid residues will be used, mostly in the one letter code form, but also in the three letter code form. Similarly recognized IUPAC nomenclature for nucleic acids will be used throughout the specification, figures and claims.
Nomenclature and Conventions for Designation of Variants In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the variants using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Thereby a number of deletions and insertions will be defined in relation to BASBPN. In FIG. 1, subtilisin 309 has 6 deletions in positions 36, 58, 158, 162, 163, and 164 in comparison to BASBPN. These deletions are in FIG. 1 indicated by asterixes (*).

The various modifications performed in a parent enzyme is indicated in general using three elements as follows:
Original Amino Acid Position Substituted Amino Acid The notation G195E thus means a substitution of a glycine in position 195 with a glutamic acid.

In the case where the original amino acid residue may be any amino acid residue, a short hand notation may at times be used indicating only the position and substituted amino acid:
Position Substituted Amino Acid Such a notation is particular relevant in connection with modification(s) in homologous subtilases (vide infra).

Similarly when the identity of the substituting amino acid residue(s) is immaterial:
Original Amino Acid Position When both the original amino acid(s) and substituted amino acid(s) may comprise any amino acid, then only the position is indicated, e.g.: 170.

When the original amino acid(s) and/or substituted amino acid(s) may comprise more than one, but not all amino acid(s), then the selected amino acids are indicated inside brackets:
Original Amino Acid Position {Substituted Amino Acid$_1$, . . . , Substituted Amino Acid$_n$}

For specific variants the specific three or one letter codes are used, including the codes Xaa and X to indicate any amino acid residue.
Substitutions:

The substitution of glutamic acid for glycine in position 195 is designated as:

Gly195Glu or G195E or the substitution of any amino acid residue acid for glycine in position 195 is designated as:

Gly195Xaa or G195X or

Gly195 or G195

The substitution of serine for any amino acid residue in position 170 would thus be designated Xaa170Ser or X170S or 170Ser or 170S Such a notation is particular relevant in connection with modification(s) in homologous subtilases (vide infra). 170Ser is thus meant to comprise e.g. both a Lys170Ser modification in BASBPN and Arg170Ser modification in BLSAVI (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.
Deletions:

A deletion of glycine in position 195 will be indicated by:

Gly195* or G195*

Correspondingly the deletion of more than one amino acid residue, such as the deletion of glycine and leucine in positions 195 and 196 will be designated Gly195*+Leu196* or G195*+L196*

Insertions:

The insertion of an additional amino acid residue such as e.g. a lysine after G195 is indicated by:

Gly195GlyLys or G195GK;

or, when more than one amino acid residue is inserted, such as e.g. a Lys, and Ala after G195 this will be indicated as:

Gly195GlyLysAla or G195GKA

In such cases the inserted amino acid residue(s) are numbered by the addition of lower case letters to the position number of the amino acid residue preceding the inserted amino acid residue(s). In the above example the sequences 194 to 196 would thus be:

|  | 194 | 195 | 195a | 195b | 196 |  |
|---|---|---|---|---|---|---|
| BLSAVI | A | - | G | - |  | L |
|  | 194 | 195 | 195a | 195b | 196 |  |
| Variant | A | - | G | - K | - A | - L (SEQ ID NO: 1) |

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

```
              194 195 196

BLSAVI        A - G - L to 194 195 195a 196

Variant       A - G - G - L        (SEQ ID NO: 2)

194 194a 195 196
```

Such instances will be apparent to the skilled person, and the indication G195GG and corresponding indications for this type of insertions are thus meant to comprise such equivalent degenerate indications.

Filling a Gap:

Where a deletion in an enzyme exists in the reference comparison with the subtilisin BPN' sequence used for the numbering, an insertion in such a position is indicated as:

*36Asp or *36D for the insertion of an aspartic acid in position 36.

Multiple Modifications:

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

| | | |
|---|---|---|
| Tyr167Gly + Arg170Gly, | | Tyr167Gly + Arg170Ala, |
| Tyr167Gly + Arg170Ser, | | Tyr167Gly + Arg170Thr, |
| Tyr167Ala + Arg170Gly, | | Tyr167Ala + Arg170Ala, |
| Tyr167Ala + Arg170Ser, | | Tyr167Ala + Arg170Thr, |
| Tyr167Ser + Arg170Gly, | | Tyr167Ser + Arg170Ala, |
| Tyr167Ser + Arg170Ser, | | Tyr167Ser + Arg170Thr, |
| Tyr167Thr + Arg170Gly, | | Tyr167Thr + Arg170Ala, |
| Tyr167Thr + Arg170Ser, | and | Tyr167Thr + Arg170Thr. |

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms*. W. H. Freeman and Company, San Francisco, Chapter 3).

Numbering of Amino Acid Positions/Residues

If nothing else is mentioned the amino acid numbering used herein correspond to that of the subtilase BPN' (BASBPN) sequence. For further description of the BPN' sequence, see FIG. 1 or Siezen et al., *Protein Engng.* 4 (1991) 719–737.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a subgroup, reflects the high pH optimum of some of the serine proteases, from pH 9.0 to 11.0 (for review, see Priest (1977) *Bacteriological Rev.* 41 711–753).

Subtilases

A sub-group of the serine proteases tentatively designated subtilases has been proposed by Siezen et al., *Protein Engng.* 4 (1991) 719–737 and Siezen et al. *Protein Science* 6 (1997) 501–523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN' (BASBPN), subtilisin Carlsberg (BLSCAR) (ALCALASE®, Novozymes A/S), and subtilisin DY (BSSDY). Other subgroup I-S1 subtilases of interest are subtilisins closely related to BSS168, such as subtilisin Amylosacchariticus (BSSAS), subtilisin J (BSAPRJ), subtilisin NAT (BSAPRN), and mesentericopeptidase (BMSAMP); subtilisins closely related to BLSCAR, such as Keratinase (BLKERA), subtilisin Carlsberg 11594 (BLSCA1), subtilisin Carlsberg 15413 (BLSCA2), subtilisin Carlsberg 14353 (BLSCA3); and the subtilisins serine protease C (BSSPRC), and serine protease D (BSSPRD), or functional variants thereof having retained the characteristic of sub-group I-S1.

A further subgroup of the subtilases, I-S2 or high alkaline subtilisins, is recognized by Siezen et al. (supra). Sub-group I-S2 proteases are described as highly alkaline subtilisins and comprises enzymes such as subtilisin PB92 (BAALKP) (MAXACAL®, Gist-Brocades NV), subtilisin 309 (BLSAVI, BLS309)(SAVINASE®, Novozymes A/S), subtilisin 147 (BLS147) (ESPERASE®, Novozymes A/S), and alkaline elastase YaB (BSEYAB). Other subgroup I-S2 subtilases of interest are subtilisin ALP I (BSAPRQ), subtilisins closely related to BLS147, such as subtilisin AprM (BSAPRM), and alkaline protease AH-101 (BAH101)), SAVINASE (BLSAVI) (or the closely related subtilisins M-protease (BSKSMK), subtilisin PB92 (BAALKP), and subtilisin BL (BLSUBL)), alkaline elastase YaB (BSEYAB), Thermitase (TVTHER), and subtilisin Sendai (BSAPRS), or functional variants thereof having retained the characteristic of sub-group I-S2.

"SAVINASE®"

SAVINASE® is marketed by NOVOZYMES A/S. It is subtilisin 309 from *B. Lentus* and differs from BAALKP only in one position (N87S, see FIG. 1 herein). SAVINASE® has the amino acid sequence designated b) in FIG. 1.

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., Nature Biotechnology, 17, 893–896 (1999). Alternatively the term "parent subtilase" may be termed "wild type subtilase".

Modification(s) of a Subtilase Variant

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant or modified gene derived from a parent microorganism which possessed an original or parent gene and which produced a corresponding parent enzyme, the parent gene having been mutated in order to produce the mutant gene from which said mutated subtilase protease is produced when expressed in a suitable host. Analogously, the mutant gene may also be derived from a parent gene produced by DNA shuffling technique.

Homologous Subtilase Sequences

The homology between two amino acid sequences is in this context described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Isolated DNA Sequence or Polynucleotide

The term "isolated nucleic acid sequence" as used herein refers to a polynucleotide molecule with a defined nucleic acid sequence, which has been isolated and purified and is thus in a form suitable for use within genetically engineered protein production systems. Such isolated molecules may be those that are separated from their natural environment and include cDNA and genomic clones as well as polynucleotides or nucleic acid sequences derived from DNA shuffling experiments or from site-directed mutagenesis experiments. Isolated polynucleotides or nucleic acid sequences of the present invention are free of other genes with which they are ordinarily associated, but may include 5' and 3' untranslated regions such as promoters and terminators. The identification of associated regions will be evident to one of ordinary skill in the art (see for example, Dynan and Tijan, Nature 316:774–78, 1985). The term "isolated nucleic acid sequence" or "isolated polynucleotides" may alternatively be termed "isolated DNA sequence, "cloned polynucleotide", "cloned nucleic acid sequence" or "cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained From

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide (amide) bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove egg stains present on the object to be cleaned during e.g. wash or hard surface cleaning. See also the "Model Detergent Wash Performance Test" in Example 3 herein.

Performance Factor

The term "Performance Factor" is defined with respect to the below formula $$P=R_{variant}-R_{parent}$$

wherein P is the Performance Factor, $R_{variant}$ is the reflectance (measured at 460 nm) of the test material after being treated with a subtilase variant as described in the "Model Detergent Wash Performance Test", and $R_{parent}$ is the reflectance (measured at 460 nm) of the test material after being treated with the corresponding parent subtilase as described in the "Model Detergent Wash Performance Test". For further details, see the "Model Detergent Wash Performance Test" in Example 3 herein.

Residual Activity

The term "Residual Activity" is defined as described in the "Ovo-inhibition Assay" herein (see Example 3).

BRIEF DESCRIPTION OF THE DRAWING

FIG. 1 shows an alignment between subtilisin BPN' (a) and SAVINASE® (b) using the GAP routine mentioned above.

DETAILED DESCRIPTION OF THE INVENTION

The present inventors have found that subtilisin variants, wherein certain regions are longer than those presently known, are inhibited by substances present in eggs, such as trypsin inhibitor type IV-0, to a significantly lesser extent than the parent subtilase and, consequently, the variants according to the invention exhibit improved wash performance with respect to removal of egg stains.

The identification thereof was done in constructing subtilisin variants, especially of the subtilisin 309 (BLSAVI or SAVINASE®). Without being limited to any specific theory it is presently believed that due to steric hindrance and/or conformational changes, binding of the egg white inhibitor in the substrate binding region of the subtilase variant is impeded.

Thus, variants which are contemplated as being suitable for the uses described herein are such variants where, when compared to the wild-type subtilase, one or more amino acid residues has been inserted in one or more of the following positions: between positions 42 and 43, between positions 51 and 52, between positions 52 and 53, between positions 53 and 54, between positions 54 and 55, between positions 55 and 56, between positions 155 and 156, between positions 156 and 157, between positions 157 and 158, between positions 158 and 159, between positions 159 and 160, between positions 160 and 161, between positions 187 and 188, between positions 188 and 189, between positions 189 and 190, between positions 216 and 217, between positions 217 and 218, or between positions 218 and 219 (BASBPN numbering), in particular between positions 217 and 218.

A subtilase variant of the first aspect of the invention may be a parent or wild-type subtilase identified and isolated from nature.

Such a parent wildtype subtilase may be specifically screened for by standard techniques known in the art.

One preferred way of doing this may be by specifically PCR amplify DNA regions known to encode active site loops in subtilases from numerous different microorganism, preferably different Bacillus strains.

Subtilases are a group of conserved enzymes, in the sense that their DNA and amino acid sequences are homologous. Accordingly it is possible to construct relatively specific primers flanking active site loops.

One way of doing this is by investigating an alignment of different subtilases (see e.g. Siezen et al. *Protein Science* 6 (1997) 501–523). It is from this routine work for a person skilled in the art to construct PCR primers flanking the positions indicated above in any of the group I-S1 or I-S2 groups, such as from BLSAVI. Using such PCR primers to amplify DNA from a number of different microorganism, preferably different Bacillus strains, followed by DNA sequencing of said amplified PCR fragments, it will be possible to identify strains which produce subtilases of these groups comprising insertions, as compared to e.g. BLSAVI sequence. Having identified the strain and a partial DNA sequence of such a subtilase of interest, it is routine work for a person skilled in the art to complete cloning, expression and purification of such a subtilase.

However, it is envisaged that a subtilase variant of the invention predominantly is a variant of a parent subtilase.

A subtilase variant suitable for the uses described herein, may be constructed by standard techniques known in the art such as by site-directed/random mutagenesis or by DNA shuffling of different subtilase sequences. See the "Material and Methods" section herein (vide infra) for further details.

As will be acknowledged by the skilled person, the variants described herein may comprise one or more further modifications, in particular one or more further insertions or substitutions.

Moreover, the insertions in the regions described herein may encompass insertion of more than just one amino acid residue. For example the variant according to the invention may contain one insertion, two insertions, or more than two insertions, such as three, four or five insertions.

In one interesting embodiment of the invention the additional amino acid residue is inserted between positions 42 and 43.

The Insertion between positions 42 and 43 is preferably selected from the group consisting of (in BASBPN numbering)

X42X{A,T,G,S}, e.g., X42XA, X42XT, X42XG, X42XS;
X42X{D,E,K,R}, e.g., X42XD, X42XE, X42XK, X42XR;
X42X{H,V,C,N,Q}, e.g., X42XH, X42XV, X42XC, X42XN, X42XQ; and
X42X{F,I,L,M,P,W,Y}, e.g., X42XF, X42XI, X42XL, X42XM, X42XP, X42XW, X42XY;

or more specific for subtilisin 309 and closely related subtilases, such as BAALKP, BLSUBL, and BSKSMK:

L42L{A,T,G,S}, e.g., L42LA, L42LT, L42LG, L42LS;
L42L{D,E,K,R}, e.g., L42LD, L42LE, L42LK, L42LR;
L42L{H,V,C,N,Q}, e.g., L42LH, L42LV, L42LC, L42LN, L42LQ; and
L42L{F,I,L,M,P,W,Y}, e.g., L42LF, L42LI, L42LL, L42LM, L42LP, L42LW, L42LY.

In a further interesting embodiment of the invention the additional amino acid residue is inserted between positions 51 and 52.

The insertion between positions 51 and 52 is preferably selected from the group consisting of (in BASBPN numbering)

X51X{A,T,G,S}, e.g., X51XA, X51XT, X51XG, X51XS;
X51X{D,E,K,R}, e.g., X51XD, X51XE, X51XK, X51XR;
X51X{H,V,C,N,Q}, e.g., X51XH, X51XV, X51XC, X51XN, X51XQ; and
X51X{F,I,L,M,P,W,Y}, e.g., X51XF, X51XI, X51XL, X51XM, X51XP, X51XW, X51XY;

or more specific for subtilisin 309 and closely related subtilases, such as BAALKP, BLSUBL, and BSKSMK:

V51V{A,T,G,S}, e.g., V51VA, V51VT, V51VG, V51VS;
V51V{D,E,K,R}, e.g., V51VD, V51VE, V51VK, V51VR;
V51V{H,V,C,N,Q}, e.g., V51VH, V51VV, V51VC, V51VN, V51VQ; and
V51V{F,I,L,M,P,W,Y}, e.g., V51VF, V51VI, V51VL, V51VM, V51VP, V51VW, V51VY.

In another interesting embodiment of the invention the additional amino acid residue is inserted between positions 52 and 53.

The insertion between positions 52 and 53 is preferably selected from the group consisting of (in BASBPN numbering)

X52X{A,T,G,S}, e.g., X52XA, X52XT, X52XG, X52XS;
X52X{D,E,K,R}, e.g., X52XD, X52XE, X52XK, X52XR;
X52X{H,V,C,N,Q}, e.g., X52XH, X52XV, X52XC, X52XN, X52XQ; and
X52X{F,I,L,M,P,W,Y}, e.g., X52XF, X52XI, X52XL, X52XM, X52XP, X52XW, X52XY;

or more specific for subtilisin 309 and closely related subtilases, such as BAALKP, BLSUBL, and BSKSMK:

P52P{A,T,G,S}, e.g., P52PA, P52PT, P52PG, P52PS;
P52P{D,E,K,R}, e.g., P52PD, P52PE, P52PK, P52PR;
P52P{H,V,C,N,Q}, e.g., P52PH, P52PV, P52PC, P52PN, P52PQ; and
P52P{F,I,L,M,P,W,Y}, e.g., P52PF, P52PI, P52PL, P52PM, P52PP, P52PW, P52PY.

In further interesting embodiment of the invention the additional amino acid residue is inserted between positions 53 and 54.

The insertion between positions 53 and 54 is preferably selected from the group consisting of (in BASBPN numbering)

X53X{A,T,G,S}, e.g., X53XA, X53XT, X53XG, X53XS;
X53X{D,E,K,R}, e.g., X53XD, X53XE, X53XK, X53XR;
X53X{H,V,C,N,Q}, e.g., X53XH, X53XV, X53XC, X53XN, X53XQ; and
X53X{F,I,L,M,P,W,Y}, e.g., X53XF, X53XI, X53XL, X53XM, X53XP, X53XW, X53XY;
or more specific for subtilisin 309 and closely related subtilases, such as BAALKP, BLSUBL, and BSKSMK:
G53G{A,T,G,S}, e.g., G53GA, G53GT, G53GG, G53GS;
G53G{D,E,K,R}, e.g., G53GD, G53GE, G53GK, G53GR;
G53G{H,V,C,N,Q}, e.g., G53GH, G53GV, G53GC, G53GN, G53GQ; and
G53G{F,I,L,M,P,W,Y}, e.g., G53GF, G53GI, G53GL, G53GM, G53GP, G53GW, G53GY.

In a still further interesting embodiment of the invention the additional amino acid residue is inserted between positions 54 and 55.

The insertion between positions 54 and 55 is preferably selected from the group consisting of (in BASBPN numbering)
X54X{A,T,G,S}, e.g., X54XA, X54XT, X54XG, X54XS;
X54X{D,E,K,R}, e.g., X54XD, X54XE, X54XK, X54XR;
X54X{H,V,C,N,Q}, e.g., X54XH, X54XV, X54XC, X54XN, X54XQ; and
X54X{F,I,L,M,P,W,Y}, e.g., X54XF, X54XI, X54XL, X54XM, X54XP, X54XW, X54XY;
or more specific for subtilisin 309 and closely related subtilases, such as BAALKP, BLSUBL, and BSKSMK:
E54E{A,T,G,S}, e.g., E54EA, E54ET, E54EG, E54ES;
E54E{D,E,K,R}, e.g., E54ED, E54EE, E54EK, E54ER;
E54E{H,V,C,N,Q}, e.g., E54EH, E54EV, E54EC, E54EN, E54EQ; and
E54E{F,I,L,M,P,W,Y}, e.g., E54EF, E54EI, E54EL, E54EM, E54EP, E54EW, E54EY.

In an even further interesting embodiment of the invention the additional amino acid residue is inserted between positions 55 and 56.

The insertion between positions 55 and 56 is preferably selected from the group consisting of (in BASBPN numbering)
X55X{A,T,G,S}, e.g., X55XA, X55XT, X55XG, X55XS;
X55X{D,E,K,R}, e.g., X55XD, X55XE, X55XK, X55XR;
X55X{H,V,C,N,Q}, e.g., X55XH, X55XV, X55XC, X55XN, X55XQ; and
X55X{F,I,L,M,P,W,Y}, e.g., X55XF, X55XI, X55XL, X55XM, X55XP, X55XW, X55XY;
or more specific for subtilisin 309 and closely related subtilases, such as BAALKP, BLSUBL, and BSKSMK:
P55P{A,T,G,S}, e.g., P55PA, P55PT, P55PG, P55PS;
P55P{D,E,K,R}, e.g., P55PD, P55PE, P55PK, P55PR;
P55P{H,V,C,N,Q}, e.g., P55PH, P55PV, P55PC, P55PN, P55PQ; and
P55P{F,I,L,M,P,W,Y}, e.g., P55PF, P55PI, P55PL, P55PM, P55PP, P55PW, P55PY.

In another interesting embodiment of the invention the additional amino acid residue is inserted between positions 155 and 156.

The insertion between positions 155 and 156 is preferably selected from the group consisting of (in BASBPN numbering)
X155X{A,T,G,S}, e.g., X155XA, X155XT, X155XG, X155XS;
X155X{D,E,K,R}, e.g., X155XD, X155XE, X155XK, X155XR;
X155X{H,V,C,N,Q}, e.g., X155XH, X155XV, X155XC, X155XN, X155XQ; and
X155X{F,I,L,M,P,W,Y}, e.g., X155XF, X155XI, X155XL, X155XM, X155XP, X155XW, X155XY;
or more specific for subtilisin 309 and closely related subtilases, such as BAALKP, BLSUBL, and BSKSMK:
N155N{A,T,G,S}, e.g., N155NA, N155NT, N155NG, N155NS;
N155N{D,E,K,R}, e.g., N155ND, N155NE, N155NK, N155NR;
N155N{H,V,C,N,Q}, e.g., N155NH, N155NV, N155NC, N155NN, N155NQ; and
N155N{F,I,L,M,P,W,Y}, e.g., N155NF, N155NI, N155NL, N155NM, N155NP, N155NW, N155NY.

In a further interesting embodiment of the invention the additional amino acid residue is inserted between positions 156 and 157.

The insertion between positions 156 and 157 is preferably selected from the group consisting of (in BASBPN numbering)
X156X{A,T,G,S}, e.g., X156XA, X156XT, X156XG, X156XS;
X156X{D,E,K,R}, e.g., X156XD, X156XE, X156XK, X156XR;
X156X{H,V,C,N,Q}, e.g., X156XH, X156XV, X156XC, X156XN, X156XQ; and
X156X{F,I,L,M,P,W,Y}, e.g., X156XF, X156XI, X156XL, X156XM, X156XP, X156XW, X156XY;
or more specific for subtilisin 309 and closely related subtilases, such as BAALKP, BLSUBL, and BSKSMK:
S156S{A,T,G,S}, e.g., S156SA, S156ST, S156SG, S156SS;
S156S{D,E,K,R}, e.g., S156SD, S156SE, S156SK, S156SR;
S156S{H,V,C,N,Q}, e.g., S156SH, S156SV, S156SC, S156SN, S156SQ; and
S156S{F,I,L,M,P,W,Y}, e.g., S156SF, S156SI, S156SL, S156SM, S156SP, S156SW, S156SY.

In a still further interesting embodiment of the invention the additional amino acid residue is inserted between positions 157 and 158.

The insertion between positions 157 and 158 is preferably selected from the group consisting of (in BASBPN numbering)
X157X{A,T,G,S}, e.g., X157XA, X157XT, X157XG, X157XS;
X157X{D,E,K,R}, e.g., X157XD, X157XE, X157XK, X157XR;
X157X{H,V,C,N,Q}, e.g., X157XH, X157XV, X157XC, X157XN, X157XQ; and
X157X{F,I,L,M,P,W,Y}, e.g., X157XF, X157XI, X157XL, X157XM, X157XP, X157XW, X157XY;
or more specific for subtilisin 309 and closely related subtilases, such as BAALKP, BLSUBL, and BSKSMK:
G157G{A,T,G,S}, e.g., G157GA, G157GT, G157GG, G157GS;
G157G{D,E,K,R}, e.g., G157GD, G157GE, G157GK, G157GR;
G157G{H,V,C,N,Q}, e.g., G157GH, G157GV, G157GC, G157GN, G157GQ; and
G157G{F,I,L,M,P,W,Y}, e.g., G157GF, G157GI, G157GL, G157GM, G157GP, G157GW, G157GY.

In an even further interesting embodiment of the invention the additional amino acid residue is inserted between positions 158 and 159.

The insertion between positions 158 and 159 is preferably selected from the group consisting of (in BASBPN numbering)
X158X{A,T,G,S}, e.g., X158XA, X158XT, X158XG, X158XS;
X158X{D,E,K,R}, e.g., X158XD, X158XE, X158XK, X158XR;

X158X{H,V,C,N,Q}, e.g., X158XH, X158XV, X158XC, X158XN, X158XQ; and
X158X{F,I,L,M,P,W,Y}, e.g., X158XF, X158XI, X158XL, X158XM, X158XP, X158XW, X158XY;
or more specific for subtilisin 309 and closely related subtilases, such as BAALKP, BLSUBL, and BSKSMK:
*158{A,T,G,S}, e.g., *158A, *158T, *158G, *158S;
*158{D,E,K,R}, e.g., *158D, *158E, *158K, *158R;
*158{H,V,C,N,Q}, e.g., *158H, *158V, *158C, *158N, *158Q; and
*158{F,I,L,M,P,W,Y}, e.g., *158F, *518I, *158L, *158M, *158P, *158W, *158Y.

In still another interesting embodiment of the invention the additional amino acid residue is inserted between positions 159 and 160.

The insertion between positions 159 and 160 is preferably selected from the group consisting of (in BASBPN numbering)
X159X{A,T,G,S}, e.g., X159XA, X159XT, X159XG, X159XS;
X159X{D,E,K,R}, e.g., X159XD, X159XE, X159XK, X159XR;
X159X{H,V,C,N,Q}, e.g., X159XH, X159XV, X159XC, X159XN, X159XQ; and
X159X{F,I,L,M,P,W,Y}, e.g., X159XF, X159XI, X159XL, X159XM, X159XP, X159XW, X159XY;
or more specific for subtilisin 309 and closely related subtilases, such as BAALKP, BLSUBL, and BSKSMK:
A159A{A,T,G,S}, e.g., A159AA, A159AT, A159AG, A159AS;
A159A{D,E,K,R}, e.g., A159AD, A159AE, A159AK, A159AR;
A159A{H,V,C,N,Q}, e.g., A159AH, A159AV, A159AC, A159AN, A159AQ; and
A159A{F,I,L,M,P,W,Y}, e.g., A159AF, A159AI, A159AL, A159AM, A159AP, A159AW, A159AY.

In a still another interesting embodiment of the invention the additional amino acid residue is inserted between positions 160 and 161.

The insertion between positions 160 and 161 is preferably selected from the group consisting of (in BASBPN numbering)
X160X{A,T,G,S}, e.g., X160XA, X160XT, X160XG, X160XS; X160X{D,E,K,R}, e.g., X160XD, X160XE, X160XK, X160XR;
X160X{H,V,C,N,Q}, e.g., X160XH, X160XV, X160XC, X160XN, X160XQ; and
X160X{F,I,L,M,P,W,Y}, e.g., X160XF, X160XI, X160XL, X160XM, X160XP, X160XW, X160XY;
or more specific for subtilisin 309 and closely related subtilases, such as BAALKP, BLSUBL, and BSKSMK:
G160G{A,T,G,S}, e.g., G160GA, G160GT, G160GG, G160GS;
G160G{D,E,K,R}, e.g., G160GD, G160GE, G160GK, G160GR;
G160G{H,V,C,N,Q}, e.g., G160GH, G160GV, G160GC, G160GN, G160GQ; and
G160G{F,I,L,M,P,W,Y}, e.g., G160GF, G160GI, G160GL, G160GM, G160GP, G160GW, G160GY.

In another interesting embodiment of the invention the additional amino acid residue is inserted between positions 187 and 188.

The insertion between positions 187 and 188 is preferably selected from the group consisting of (in BASBPN numbering)
X187X{A,T,G,S}, e.g., X187XA, X187XT, X187XG, X187XS;
X187X{D,E,K,R}, e.g., X187XD, X187XE, X187XK, X187XR;
X187X{H,V,C,N,Q}, e.g., X187XH, X187XV, X187XC, X187XN, X187XQ; and
X187X{F,I,L,M,P,W,Y}, e.g., X187XF, X187XI, X187XL, X187XM, X187XP, X187XW, X187XY;
or more specific for subtilisin 309 and closely related subtilases, such as BAALKP, BLSUBL, and BSKSMK:
A187A{A,T,G,S}, e.g., A187AA, A187AT, A187AG, A187AS;
A187A{D,E,K,R}, e.g., A187AD, A187AE, A187AK, A187AR;
A187A{H,V,C,N,Q}, e.g., A187AH, A187AV, A187AC, A187AN, A187AQ; and
A187A{F,I,L,M,P,W,Y}, e.g., A187AF, A187AI, A187AL, A187AM, A187AP, A187AW, A187AY.

In a further interesting embodiment of the invention the additional amino acid residue is inserted between positions 188 and 189.

The insertion between positions 188 and 189 is preferably selected from the group consisting of (in BASBPN numbering)
X188X{A,T,G,S}, e.g., X188XA, X188XT, X188XG, X188XS;
X188X{D,E,K,R}, e.g., X188XD, X188XE, X188XK, X188XR;
X188X{H,V,C,N,Q}, e.g., X188XH, X188XV, X188XC, X188XN, X188XQ; and
X188X{F,I,L,M,P,W,Y}, e.g., X188XF, X188XI, X188XL, X188XM, X188XP, X188XW, X188XY;
or more specific for subtilisin 309 and closely related subtilases, such as BAALKP, BLSUBL, and BSKSMK:
S188S{A,T,G,S}, e.g., S188SA, S188ST, S188SG, S188SS;
S188S{D,E,K,R}, e.g., S188SD, S188SE, S188SK, S188SR;
S188S{H,V,C,N,Q}, e.g., S188SH, S188SV, S188SC, S188SN, S188SQ; and
S188S{F,I,L,M,P,W,Y}, e.g., S188SF, S188SI, S188SL, S188SM, S188SP, S188SW, S188SY.

In a still further interesting embodiment of the invention the additional amino acid residue is inserted between positions 189 and 190.

The insertion between positions 189 and 190 is preferably selected from the group consisting of (in BASBPN numbering)
X189X{A,T,G,S}, e.g., X189XA, X189XT, X189XG, X189XS;
X189X{D,E,K,R}, e.g., X189XD, X189XE, X189XK, X189XR;
X189X{H,V,C,N,Q}, e.g., X189XH, X189XV, X189XC, X189XN, X189XQ; and
X189X{F,I,L,M,P,W,Y}, e.g., X189XF, X189XI, X189XL, X189XM, X189XP, X189XW, X189XY;
or more specific for subtilisin 309 and closely related subtilases, such as BAALKP, BLSUBL, and BSKSMK:
F189F{A,T,G,S}, e.g., F189FA, F189FT, F189FG, F189FS;
F189F{D,E,K,R}, e.g., F189FD, F189FE, F189FK, F189FR;
F189F{H,V,C,N,Q}, e.g., F189FH, F189FV, F189FC, F189FN, F189FQ; and
F189F{F,I,L,M,P,W,Y}, e.g., F189FF, F189FI, F189FL, F189FM, F189FP, F189FW, F189FY.

In another interesting embodiment of the invention the additional amino acid residue is inserted between positions 216 and 217.

The insertion between positions 216 and 217 is preferably selected from the group consisting of (in BASBPN numbering)

X216X{A,T,G,S}, e.g., X216XA, X216XT, X21GXG, X216XS;
X216X{D,E,K,R}, e.g., X216XD, X216XE, X216XK, X216XR;
X216X{H,V,C,N,Q}, e.g., X216XH, X21GXV, X216XC, X216XN, X216XQ; and
X216X{F,I,L,M,P,W,Y}, e.g., X216XF, X216XI, X216XL, X216XM, X216XP, X216XW, X216XY;
or more specific for subtilisin 309 and closely related subtilases, such as BAALKP, BLSUBL, and BSKSMK:
S216S{A,T,G,S}, e.g., S216SA, S216ST, S216SG, S216SS;
S216S{D,E,K,R}, e.g., S216SD, S216SE, S216SK, S216SR;
S216S{H,V,C,N,Q}, e.g., S216SH, S216SV, S216SC, S216SN, S216SQ; and
S216S{F,I,L,M,P,W,Y}, e.g., S216SF, S216SI, S216SL, S216SM, S216SP, S216SW, S216SY.

In another interesting embodiment of the invention the additional amino acid residue is inserted between positions 217 and 218.

The insertion between positions 217 and 218 is preferably selected from the group consisting of (in BASBPN numbering)
X217X{A,T,G,S}, e.g., X217XA, X217XT, X217XG, X217XS;
X217X{D,E,K,R}, e.g., X217XD, X217XE, X217XK, X217XR;
X217X{H,V,C,N,Q}, e.g., X217XH, X217XV, X217XC, X217XN, X217XQ; and
X217X{F,I,L,M,P,W,Y}, e.g., X217XF, X217XI, X217XL, X217XM, X217XP, X217XW, X217XY;
or more specific for subtilisin 309 and closely related subtilases, such as BAALKP, BLSUBL, and BSKSMK:
L217L{A,T,G,S}, e.g., L217LA, L217LT, L217LG, L217LS;
L217L{D,E,K,R}, e.g., L217LD, L217LE, L217LK, L217LR;
L217L{H,V,C,N,Q}, e.g., L217LH, L217LV, L217LC, L217LN, L217LQ; and
L217L{F,I,L,M,P,W,Y}, e.g., L217LF, L217LI, L217LL, L217LM, L217LP, L217LW, L217LY.

In still another interesting embodiment of the invention the additional amino acid residue is inserted between positions 218 and 219.

The insertion between positions 218 and 219 is preferably selected from the group consisting of (in BASBPN numbering)
X218X{A,T,G,S}, e.g., X218XA, X218XT, X218XG, X218XS;
X218X{D,E,K,R}, e.g., X218XD, X218XE, X218XK, X218XR;
X218X{H,V,C,N,Q}, e.g., X218XH, X218XV, X218XC, X218XN, X218XQ; and
X218X{F,I,L,M,P,W,Y}, e.g., X218XF, X218XI, X218XL, X218XM, X218XP, X218XW, X218XY;
or more specific for subtilisin 309 and closely related subtilases, such as BAALKP, BLSUBL, and BSKSMK:
N218N{A,T,G,S}, e.g., N218NA, N218NT, N218NG, N218NS;
N218N{D,E,K,R}, e.g., N218ND, N218NE, N218NK, N218NR;
N218N{H,V,C,N,Q}, e.g., N218NH, N218NV, N218NC, N218NN, N218NQ; and
N218N{F,I,L,M,P,W,Y}, e.g., N218NF, N218NI, N218NL, N218NM, N218NP, N218NW, N218NY.

Moreover, it is contemplated that, in addition to the above-mentioned insertions performed in accordance with the invention, insertion of at least one additional amino acid residue in the active site loop (b) region from position 95 to 103 (BASBPN numbering) will further reduce the tendency towards inhibition by trypsin inhibitor type IV-0. It is envisaged that additional insertions between position 98 and 99 and/or insertions between positions 99 and 100 will be particular beneficial. Examples of such additional insertions are:
X98X{A,T,G,S}, e.g., X98XA, X98XT, X98XG, X98XS;
X98X{D,E,K,R}, e.g., X98XD, X98XE, X98XK, X98XR;
X98X{H,V,C,N,Q}, e.g., X98XH, X98XV, X98XC, X98XN, X98XQ; and
X98X{F,I,L,M,P,W,Y}, e.g., X98XF, X98XI, X98XL, X98XM, X98XP, X98XW, X98XY; preferably X98XD and X98XE;
or more specific for subtilisin 309 and closely related subtilases:
A98A{A,T,G,S}, e.g., A98AA, A98AT, A98AG, A98AS;
A98A{D,E,K,R}, e.g., A98AD, A98AE, A98AK, A98AR;
A98A{H,V,C,N,Q}, e.g., A98AH, A98AV, A98AC, A98AN, A98AQ;
A98A{F,I,L,M,P,W,Y}, e.g., A98AF, A98AI, A98AL, A98AM, A98AP, A98AW, A98AY; preferably A98AD and A98AE.

Further examples include:
X99X{A,T,G,S}, e.g., X99XA, X99XT, X99XG, X99XS;
X99X{D,E,K,R}, e.g., X99XD, X99XE, X99XK, X99XR;
X99X{H,V,C,N,Q}, e.g., X99XH, X99XV, X99XC, X99XN, X99XQ; and
X99X{F,I,L,M,P,W,Y}, e.g., X99XF, X99XI, X99XL, X99XM, X99XP, X99XW, X99XY; preferably X99XD and X99XE;
or more specific for subtilisin 309 and closely related subtilases:
S99S{A,T,G,S}, e.g., S99SA, S99ST, S99SG, S99SS;
S99S{D,E,K,R}, e.g., S99SD, S99SE, S99SK, S99SR;
S99S{H,V,C,N,Q}, e.g., S99SH, S99SV, S99SC, S99SN, S99SQ;
S99S{F,I,L,M,P,W,Y}, e.g., S99SF, S99SI, S99SL, S99SM, S99SP, S99SW, S99SY; preferably S99SD and S99SE.

With respect to insertions between position 99 and 100, it is preferred that the insertion is combined with a substitution in position 99. Thus, in addition to the contemplated insertions mentioned above, the following substitutions in position 99 are considered relevant:
X99{A,T,G,S}, e.g., X99A, X99T, X99G, X99S;
X99{D,E,K,R}, e.g., X99D, X99E, X99K, X99R;
X99{H,V,C,N,Q}, e.g., X99H, X99V, X99C, X99N, X99Q; and
X99{F,I,L,M,P,W,Y} e.g., X99F, X99I, X99L, X99M, X99P, X99W, X99Y;
or more specific for subtilisin 309 and closely related subtilases:
S99{A,T,G}, e.g., S99A, S99T, S99G;
S99{D,E,K,R}, e.g., S99D, S99E, S99K, S99R;
S99{H,V,C,N,Q}, e.g., S99H, S99V, S99C, S99N, S99Q; and
S99{F,I,L,M,P,W,Y}, e.g., S99F, S99I, S99L, S99M, S99P, S99W, S99SY.

In a preferred embodiment the substitution in position 99 is selected from the group consisting of X99{A,T,G,S}, in particular X99A, or more specific for subtilisin 309 and closely related subtilases: S99{A,T,G}, in particular S99A.

It is well known in the art that a so-called conservative substitution of one amino acid residue to a similar amino acid residue is expected to produce only a minor change in the characteristic of the enzyme.

Table I below list groups of conservative amino acid substitutions.

TABLE I

Conservative amino acid substitutions

| Common Property | Amino Acid |
| --- | --- |
| Basic (positive charge) | K = lysine |
|  | H = histidine |
| Acidic (negative charge) | E = glutamic acid |
|  | D = aspartic acid |
| Polar | Q = glutamine |
|  | N = asparagine |
| Hydrophobic | L = leucine |
|  | I = isoleucine |
|  | V = valine |
|  | M = methionine |
| Aromatic | F = phenylalanine |
|  | W = tryptophan |
|  | Y = tyrosine |
| Small | G = glycine |
|  | A = alanine |
|  | S = serine |
|  | T = threonine |

According to this principle subtilase variants comprising conservative substitutions are expected to exhibit characteristics that are not drastically different from each other.

Based on the disclosed and/or exemplified subtilase variants herein, it is routine work for a person skilled in the art to identify suitable conservative modification(s) to these variants in order to obtain other subtilase variants exhibiting similarly improved wash-performance.

It is preferred that the parent subtilase belongs to the subgroups I-S1 and I-S2, especially subgroup I-S2, both for isolating enzymes from nature or from the artificial creation of diversity, and for designing and producing variants from a parent subtilase.

In relation to variants from subgroup I-S1, it is preferred to select a parent subtilase from the group consisting of BSS168 (BSSAS, BSAPRJ, BSAPRN, BMSAMP), BASBPN, BSSDY, BLSCAR (BLKERA, BLSCA1, BLSCA2, BLSCA3), BSSPRC, and BSSPRD, or functional variants thereof having retained the characteristic of sub-group I-S1.

In relation to variants from subgroup I-S2 it is preferred to select a parent subtilase from the group consisting of BSAPRQ, BLS147 (BSAPRM, BAH101), BLSAVI (BSKSMK, BAALKP (BAPB92), BLSUBL), BSEYAB, TVTHER, and BSAPRS, or functional variants thereof having retained the characteristic of sub-group I-S2.

In particular, the parent subtilase is BLSAVI (SAVINASE®, NOVOZYMES A/S), and a preferred subtilase variant of the invention is accordingly a variant of SAVINASE®.

The present invention also encompasses any of the above mentioned subtilase variants in combination with any other modification to the amino acid sequence thereof. Especially combinations with other modifications known in the art to provide improved properties to the enzyme are envisaged. The art describes a number of subtilase variants with different improved properties and a number of those are mentioned in the "Background of the invention" section herein (vide supra). Those references are disclosed here as references to identify a subtilase variant, which advantageously can be combined with a subtilase variant described herein.

Such combinations comprise the positions: 222 (improves oxidation stability), 218 (improves thermal stability), substitutions in the Ca-binding sites stabilizing the enzyme, e.g. position 76, and many other apparent from the prior art.

In further embodiments a subtilase variant described herein may advantageously be combined with one or more modification(s) in any of the positions (BASBPN numbering):

27, 36, 56, 76, 87, 95, 96, 97, 98, 99, 100, 101, 102, 103, 104, 120, 123, 129, 131, 132, 133, 143, 159, 167, 170, 192, 194, 206, 217, 218, 222, 224, 232, 235, 236, 245, 248, 252 or 274

Specifically, the following variants of the subtilisins SAVINASE (BLSAVI), BLSUBL, BSKSMK, and BAALKP are considered appropriate for combination: K27R, *36D, T56P, N76D, N87S, A97N, A98AT, A98AS, N99ND, N99NR, N99A, N99T, R101G, P103A, V104A, V104I, V104N, V104Y, D120H, N123S, P129K, P131H, A133P, A133D, A133E, T143K, *159D, *159E, Y167X, Y167A, R170X, R170S, A194P, Q206E, F217R, N218S, M222S, M222A, T224S, A232V, K235L, Q236H, Q245R, N248D, N252K and T274A.

Of further particular interest are variants of the subtilase of the invention, wherein the modifications comprise any of the modifications R101G+V104N, S101G+V104N, S87N+S101G+V104N, K27R+V104Y+N123S+T274A, N76D+V104A, or R101G+P103A+V104I+*159D+A232V+Q236H+Q245R+N248D+N252K; or other combinations of these modifications (K27R, N76D, R101G, S101G, P103A, V104I, V104N, V104A, V104Y, N123S, *159D, A232V, Q236H, Q245R, N248D, N252K T274A), in combination with any one or more of the modification(s) indicated above or below exhibit improved properties.

A particular interesting variant is a variant, which, in addition to the insertions according to the invention, contains the following substitutions: S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

As mentioned above, the variants of the invention are only inhibited by trypsin inhibitor type IV-0 to a limited extent and, consequently, they exhibit excellent wash performance on egg stains. Therefore, in order to enable the skilled person—at an early stage of his development work—to select effective and preferred variants for this purpose, the present inventors have provided a suitable preliminary test, which can easily be carried out by the skilled person in order to initially assess the performance of the variant in question.

Thus, the "Ovo-inhibition Assay" disclosed in Example 4 herein may be employed to initially assess the potential of a selected variant. In other words, the "Ovo-inhibition Assay" may be employed to assess whether a selected variant will be inhibited, and to what extent, by the trypsin inhibitor type IV-0. Using this test, the suitability of a selected variant to remove egg stains can be assessed, the rationale being that if a selected variant is strongly inhibited by trypsin inhibitor type IV-0, it is normally not necessary to carry out further test experiments.

Therefore, a variant which is particular interesting for the purposes described herein, is a variant which—when tested in the "Ovo-inhibition Assay" described in Example 4 herein—has a Residual Activity of at least 15%, such as at least 20%, preferably at least 25%, such as at least 30%, more preferably at least 35%. In a particular interesting embodiment of the invention, the variant has a Residual Activity of at least 40%, such as at least 45%, e.g. at least 50%, preferably at least 55%, such as at least 60%, more preferably at least 65%, such as at least 70%, even more preferably at least 75%, such as at least 80%, e.g. at least 90%, when tested in the "Ovo-inhibition Assay" described in Example 4 herein.

Evidently, it is preferred that the variant of the invention fulfils the above criteria on at least the stated lowest level, more preferably at the stated intermediate level and most preferably on the stated highest level.

Alternatively, or in addition to the above-mentioned assay, the suitability of a selected variant may be tested in the "Model Detergent Wash Performance Test" disclosed in Example 3 herein. The "Model Detergent Wash Perfomance Test" may be employed to assess the ability of a variant, when incorporated in a standard detergent composition, to remove egg stains from a standard textile as compared to a reference system, namely the parent subtilase (incorporated in the same model detergent system and tested under identical conditions). Using this test, the suitability of a selected variant to remove egg stains can be initially investigated, the rationale being that if a selected variant does not show a significant improvement in the test compared to the parent subtilase, it is normally not necessary to carry out further test experiments.

Therefore, variants which are particular interesting for the purposes described herein, are such variants which, when tested in a model detergent composition comprising 6.2% LAS (Nansa 80S)
    2% Sodium salt of $C_{16}$–$C_{18}$ fatty acid
    4% Non-ionic surfactant (Plurafax LF404)
    22% Zeolite P
    10.5% $Na_2CO_3$
    4% $Na_2Si_2O_5$
    2% Carboxymethylcellulose (CMC)
    6.8% Acrylate liquid CP5 40%
    20% Sodium perborate (empirical formula $NaBO_2.H_2O_2$)
    0.2% EDTA
    21% $Na_2SO_4$
    Water (balance)

as described in the "Model Detergent Wash Performance Test" herein, shows an improved wash performance on egg stains as compared to the parent subtilase tested under identical conditions.

The improvement in the wash performance may be quantified by employing the so-called "Performance Factor" defined in Example 3, herein.

In a very interesting embodiment of the invention, the variant of the invention, when tested in the "Wash Performance Test" has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the variant of the invention fulfils the above criteria on at least the stated lowest level, more preferably at the stated intermediate level and most preferably on the stated highest level.

Producing a Subtilase Variant

Many methods for cloning a subtilase and for introducing insertions into genes (e.g. subtilase genes) are well known in the art, cf. the references cited in the "BACKGROUND OF THE INVENTION" section.

In general standard procedures for cloning of genes and introducing insertions (random and/or site directed) into said genes may be used in order to obtain a subtilase variant of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further, a subtilase variant may be constructed by standard techniques for artificial creation of diversity, such as by DNA shuffling of different subtilase genes (WO 95/22625; Stemmer WPC, Nature 370:389–91 (1994)). DNA shuffling of e.g. the gene encoding SAVINASE® with one or more partial subtilase sequences identified in nature to comprise insertion(s) in any of the indicated positions in comparison to BLSAVI (SAVINASE®), will after subsequent screening in the ovo-inhibitor assay, provide subtilase variants suitable for the purposes described herein.

Expression Vectors

A recombinant expression vector comprising a DNA construct encoding the enzyme of the invention may be any vector that may conveniently be subjected to recombinant DNA procedures.

The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid.

Alternatively, the vector may be one that on introduction into a host cell is integrated into the host cell genome in part or in its entirety and replicated together with the chromosome(s) into which it has been integrated.

The vector is preferably an expression vector in which the polynucleotide encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any polynucleotide with a sequence, which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a polynucleotide enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The polynucleotide with a DNA sequence encoding the present enzyme and introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, or gram-negative bacteria such as *Echerichia coli*.

The transformation of the bacteria may be effected by protoplast transformation, electroporation, conjugation, or by using competent cells in a manner known per se (cf. Sambrook et al., (supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method For Producing a Subtilase Variant

The present invention provides a method of producing an isolated enzyme according to the invention, wherein a suitable host cell, which has been transformed with a polynucleotide with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context, homologous impurities, means any impurities (e.g. other polypeptides than the enzyme of the invention) that originate from the homologous cell from which the enzyme of the invention is originally obtained.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Cleaning and Detergent Compositions

In general, cleaning and detergent compositions are well described in the art and reference is made to WO 96/34946; WO 97/07202; WO 95/30011 for further description of suitable cleaning and detergent compositions.

Furthermore the examples herein demonstrate the improvements in wash performance on egg stains for a number of subtilase variants.

Detergent Compositions

The subtilase variant may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising a subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, SAVINASE™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases:

Suitable lipases include those of bacterial or fungal origin. Chemically modified or protein engineered mutants are included. Examples of useful lipases include lipases from Humicola (synonym Thermomyces), e.g. from H. lanuginosa (T. lanuginosus) as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g. from B. subtilis (Dartois et al. (1993), Biochemica et Biophysica Acta, 1131, 253–360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases:

Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of B. licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. No. 4,435,307, No. 5,648,263, No. 5,691,178, No. 5,776,757 and WO 89/09259.

Especially suitable cellulases are the alkaline or neutral cellulases having co lour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, No. 5,686,593, No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from Coprinus, e.g. from C. cinereus, and variants thereof as those described in WO 93/24618, NWO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition typically comprises one or more surfactants, which may be non-ionic including semi-polar and/or anionic and/or cationic and/or zwitterionic. The surfactants are typically present at a level of from 0.1% to 60% by weight. When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinylpyridine-N-oxide), poly (vinylimidazole), polycarboxylates such as polyacrylates, maleic/acrylic acid copolymers and lauryl methacrylate/acrylic acid copolymers.

The detergent may contain a bleaching system that may comprise a $H_2O_2$ source such as perborate or percarbonate that may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202, which is hereby incorporated as reference.

The invention is described in further detail in the following examples, which are not in any way intended to limit the scope of the invention as claimed.

In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1X}$–$C_{1Y}$ alkyl sulfate
SS: Secondary soap surfactant of formula 2-butyl octanoic acid
25EY: A $C_{12}$–$C_{15}$ predominantly linear primary alcohol condensed with an average of Y moles of ethylene oxide
45EY: A $C_{14}$–$C_{15}$ predominantly linear primary alcohol condensed with an average of Y moles of ethylene oxide
XYEZS: $C_{1X}$–$C_{1Y}$ sodium alkyl sulfate condensed with an average of Z moles of ethylene oxide per mole
Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF GmbH
CFAA: $C_{12}$–$C_{14}$ alkyl N-methyl glucamide
TFAA: $C_{16}$–$C_{18}$ alkyl N-methyl glucamide
Silicate: Amorphous Sodium Silicate ($SiO_2$:$Na_2O$ ratio=2.0)
NaSKS-6: Crystalline layered silicate of formula δ-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12}.27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2.H_2O_2$
PB4: Anhydrous sodium perborate tetrahydrate
Percarbonate: Anhydrous sodium percarbonate bleach of empirical formula $2Na_2CO_3.3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylene diamine-N,N'-disuccinic acid, [S,S] isomer in the form of the sodium salt
Suds 25% paraffin wax Mpt 50° C., 17% hydrophobic silica, Suppressor: 58% paraffin oil
Granular Suds 12% Silicone/silica, 18% stearyl alcohol, 70%
suppressor: starch in granular form
Sulphate: Anhydrous sodium sulphate
HMWPEO: High molecular weight polyethylene oxide
TAE 25: Tallow alcohol ethoxylate (25)

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulphonate | 0.1 |
| Minors up to 100% | |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |

-continued

| | |
|---|---|
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention, which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinylimidazole and vinylpyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl hydroxy ethyl ammonium chloride | — | 3.0 |
| Smectite clay | — | 5.0 |
| PVP | 2.0 | — |
| Water / Minors | Up to 100% | |

| Powder automatic dishwash composition I | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |
| Powder automatic dishwash composition II | |
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |
| Powder automatic dishwash composition III | |
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |

-continued

| | |
|---|---|
| Tetraacetyl ethylene diamine (TAED) | 0–6% |
| Maleic acid/acrylic acid copolymer | 0–5% |
| Clay | 1–3% |
| Polyamino acids | 0–20% |
| Sodium polyacrylate | 0–8% |
| Enzymes | 0.0001–0.1% |
| Powder automatic dishwash composition IV | |
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |
| Powder automatic dishwash composition V | |
| Nonionic surfactant | 1–7% |
| Sodium disilicate | 18–30% |
| Trisodium citrate | 10–24% |
| Sodium carbonate | 12–20% |
| Monopersulphate (2 $KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |
| Powder and liquid dishwash composition with cleaning surfactant system VI | |
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |
| 70:30 wt. C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |
| Non-aqueous liquid automatic dishwshing composition VII | |
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |
| Non-aqueous liquid dishwashing composition VIII | |
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |
| Thixotropic liquid automatic dishwashing composition IX | |
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |
| Liquid automatic dishwashing composition X | |
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |
| Liquid automatic dishwashing composition containing protected bleach particles XI | |
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |

-continued

| Enzymes | 0.0001–0.1% |
|---|---|
| Water | Balance |

XII: Automatic dishwashing compositions as described in I, II, III, IV, VI and X, wherein perborate is replaced by percarbonate.

XIII: Automatic dishwashing compositions as described in I–VI, which additionally contain a manganese catalyst. The manganese catalyst may, e.g., be one of the compounds described in "Efficient manganese catalysts for low-temperature bleaching", Nature, (1994), 369, 637–639.

Materials and Methods
Textiles:
WFK10N standard textile pieces (egg stains) were obtained from WFK Testgewebe GmbH, Christenfeld 10, D-41379 Brüggen-Bracht, Germany.

Strains:
B. subtilis DN1885 (Diderichsen et al., 1990).
B. lentus 309 and 147 are specific strains of Bacillus lentus, deposited with the NCIB and accorded the accession numbers NCIB 10309 and 10147, and described in U.S. Pat. No. 3,723,250 incorporated by reference herein.
E. coli MC 1000 (M. J. Casadaban and S. N. Cohen (1980); J. Mol. Biol. 138 179–207), was made $r^-,m^+$ by conventional methods and is also described in U.S. patent application Ser. No. 039,298.

Plasmids:
pJS3: E. coli—B. subtilis shuttle vector containing a synthetic gene encoding for subtilase 309 (Described by Jacob Schiødt et al. in Protein and Peptide letters 3:39–44 (1996)).
pSX222: B. subtilis expression vector (described in WO 96/34946).

General Molecular Biology Methods:
Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes For DNA Manipulations
Unless otherwise mentioned all enzymes for DNA manipulations, such as e.g. restiction endonucleases, ligases etc., are obtained from New England Biolabs, Inc.

Proteolytic Activity
In the context of this invention proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novozymes A/S, Denmark, which folder is hereby included by reference.

A GU is a Glycine Unit, defined as the proteolytic enzyme activity which, under standard conditions, during a 15 minutes' incubation at 40° C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

Fermentation:
Fermentations for the production of subtilase enzymes were performed at 30° C. on a rotary shaking table (300 r.p.m.) in 500 ml baffled Erlenmeyer flasks containing 100 ml BPX medium for 5 days.

Consequently in order to make an e.g. 2 liter broth 20 Erlenmeyer flasks were fermented simultaneously.

Media:

| BPX Medium Composition (per liter) | |
|---|---|
| Potato starch | 100 g |
| Ground barley | 50 g |
| Soybean flour | 20 g |
| $Na_2HPO_4 \times 12\ H_2O$ | 9 g |
| Pluronic | 0.1 g |
| Sodium caseinate | 10 g |

The starch in the medium is liquefied with α-amylase and the medium is sterilized by heating at 120° C. for 45 minutes. After sterilization the pH of the medium is adjusted to 9 by addition of $NaHCO_3$ to 0.1 M.

EXAMPLE 1

Construction and Expression of Enzyme Variants:
Site-Directed Mutagenesis:
Subtilase 309 (SAVINASE®) site-directed variants of the invention comprising specific insertions and comprising specific substitutions were made by traditional cloning of DNA fragments (Sambrook et al., Molecular Cloning: A Laboratory Manual, 2nd Ed., Cold Spring Harbor, 1989) produced by PCR with oligos containing the desired insertions (see below).

The template plasmid DNA was pJS3 (see below), or an analogue of this containing a variant of Subtilase 309.

Insertions and substitutions were introduced by oligo directed mutagenesis to the construction of variants.

The Subtilase 309 variants were transformed into E. coli. DNA purified from a over night culture of these transformants were transformed into B. subtilis by restriction endonuclease digestion, purification of DNA fragments, ligation, transformation of B. subtilis. Transformation of B. subtilis was performed as described by Dubnau et al., 1971, J. Mol. Biol. 56, pp. 209–221.

Site-Directed Mutagenesis in Order to Introduce Insertions and Substitutions in a Specific Region:
The overall strategy to used to perform site-directed mutagenesis was:
Mutagenic primers (oligonucleotides) were synthesized corresponding to the DNA sequence flanking the sites of insertion and substitutions, separated by the DNA base pairs defining the insertions and substitutions.

Subsequently, the resulting mutagenic primers were used in a PCR reaction with the modified plasmid pJS3 (see above). The resulting PCR fragment was purified and extended in a second PCR-reaction, the resulting PCR product was purified and extended in a third PCR-reaction before being digested by endonucleases and cloned into the E. coli-B. subtilis shuttle vector (see below). The PCR reactions are performed under normal conditions.

Following this strategy two insertion and one substitution was constructed in SAVINASE® wherein insertions was introduced in position 99 (*99aD) and 217 (*217aP) respectively and a substitution was introduced in position S99A (see below).

The insertion and substitution at position 99 was introduced by a mutagenic primer (5' CCG AAC CTG AAC CAT CCG CGG CCC CTA GGA CTT TAA CAG C 3' (sense) (SEQ ID NO: 3) ) were used in a PCR reaction with an opposite primer (5' GAG TTA AGC CCA GAA GAT GTG GAC GCG 3' (antisense) (SEQ ID NO: 4)).

The produced PCR fragment were extended towards the C-terminal of SAVINASE by a second round of PCR introducing the insertion at position 217 with primer 5' CAT CGA TGT ACC GTT TGG TAA GCT GGC ATA TGT TG 3' (SEQ ID NO: 5). The second round PCR product were extended towards the C-terminal of SAVINASE by a third round of PCR with primer; 5' AAC CGC ACA GCG TTT TTT TAT TGA TTA ACG CGT TGC 3' (SEQ ID NO: 6), situated downstream at the Mlu I site in pJS3. All PCR reactions used plasmid pJS3 as template. The extended DNA-fragment resulting from third round PCR was cloned into the Sal I- and Mlu I-sites of the modified plasmid pJS3 (see above).

The plasmid DNA was transformed into *E. coli* by well-known techniques and one *E. coli* colony were sequenced to confirm the mutation designed.

In order to purify a subtilase variant of the invention, the *B. subtilis* pJS3 expression plasmid comprising a variant of the invention was transformed into a competent *B. subtilis* strain and was fermented as described above in a medium containing 10 µg/ml Chloramphenicol (CAM).

EXAMPLE 2

Purification of Enzyme Variants:

This procedure relates to purification of a 2 liter scale fermentation for the production of the subtilases of the invention in a Bacillus host cell.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 M dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 M calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of Subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and fermentation, and the above isolation procedure the following subtilisin 309 variants were produced and isolated:

L42LN+P129PA
S99SD+L42LN
L42LN+L217LP
L42LN+S99SD+P129PA
S99A+S99SD+N155NA=S99AD+N155NA
S99A+S99SD+N155ND=S99AD+N155ND
S99A+S99SD+N155NR=S99AD+N155NR
S99A+S99SD+N155NF=S99AD+N155NF
S99A+S99SD+S188SE=S99AD+S188SE
S99A+S99SD+S188SD=S99AD+S188SD
S99A+S99SD+S188SK=S99AD+S188SK
S99A+S99SD+S188SL=S99AD+S188SL
S99A+S99SD+S188SA=S99AD+S188SA
S99A+S99SD+S216SP=S99AD+S216SP
S99A+S99SD+S216SDP=S99AD+S216SDP
S99A+S99SD+S216SPD=S99AD+S216SPD
S99D+S101R+S103A+V104I+G160S+A194P+V199M+V205I+S216SD
S99D+S101R+S103A+V104I+G160S+A194P+V199M+V205I+S216SE
L217LP
L217LA
L217LDP
S99SD+L217LP
P129PA+L217LP
S99A+S99SD+L217LP=S99AD+L217LP
S99A+S99SD+L217LDP=S99AD+L217LDP
S99A+S99SD+L217LPD=S99AD+L217LPD
S99D+S101R+S103A+V104I+G160S+A194P+V199M+V205I+L217LD
S99D+S101R+S103A+V104I+G160S+A194P+V199M+V205I+L217LE
S99A+S99SD+N218NP=S99AD+N218NP
S99A+S99SD+N218NDP=S99AD+N218NDP
S99A+S99SD+N218NPD=S99AD+N218NPD

EXAMPLE 3

The "Model Detergent Wash Performance Test":

In order to asses the wash performance of selected subtilase variants in a standard detergent composition, standard washing experiments may be performed using the below experimental conditions:

| Detergent: | Model detergent |
|---|---|
| Detergent dosage | 4.0 g/l |
| pH | 10.1 |
| Wash time | 20 min |
| Temperature: | 30° C. |
| Water hardness: | 15° dH |
| Enzyme concentration: | 10 nm (in the detergent solution) |
| Test system: | 10 ml beakers with a stirring rod |
| Textile/volume: | 5 textile pieces (∅ 2.5 cm)/50 ml detergent solution |
| Test material: | WFK10N (egg stains) |

The composition of the model detergent is as follows:

6.2% LAS (Nansa 80S)

2% Sodium salt of $C_{16}$–$C_{18}$ fatty acid

4% Non-ionic surfactant (Plurafax LF404)

22% Zeolite P 10.5% $Na_2CO_3$

4% $Na_2Si_2O_5$

2% Carboxymethylcellulose (CMC)

6.8% Acrylate liquid CP5 40%

20% Sodium perborate (empirical formula $NaBO_2.H_2O_2$)

0.2% EDTA

21% Na$_2$SO$_4$

Water (balance)

pH of the detergent solution is adjusted to 10.1 by addition of HCl or NaOH. Water hardness is adjusted to 15° dH by addition of CaCl$_2$ and MGCl$_2$ (Ca$^{2+}$:Mg$^{2+}$=4:1) to the test system. After washing the textile pieces are flushed in tap water and air-dried.

Measurement of the reflectance ($R_{variant}$) on the test material is performed at 460 nm using a Macbeth ColorEye 7000 photometer (Macbeth, Division of Kollmorgen Instruments Corporation, Germany). The measurements are performed accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of the parent enzyme is tested. The subsequent measurement of the reflectance ($R_{parent}$) is performed as described right above.

The wash performance is evaluated by means of the Performance Factor (P) which is defined in accordance with the below formula:

$$P = (R_{variant} - R_{blank}) - (R_{parent} - R_{blank})$$
$$= R_{variant} - R_{parent}.$$

EXAMPLE 4

The "Ovo-Inhibition Assay"

The below inhibition assay is based on the principle that the subtilase variant to be tested will catalyse the hydrolysis of a peptide-pNA bond, thereby releasing the yellow pNA, which may conveniently be followed at 405 nm. The amount of released pNA after a given period of time is a direct measure of the subtilase activity. By carrying out such hydrolysis experiments with and without inhibitor, respectively, it is possible to obtain a quantitative measure for the degree to which a certain subtilase variant is inhibited.

| Reaction conditions: | |
|---|---|
| Enzyme concentration: | 0.0003 mg/ml |
| Conc. of trypsin inhibitor type IV-0: | 0.0015 mg/ml |
| Initial substrate concentration: | 0.81 mM |
| Reaction time: | 11 min |
| Assay temperature: | 25° C. |
| Assay pH: | 8.6 |
| Absorbance measured at: | 405 nm |

Assay Solutions:

Substrate Solution (2 mM):

500 mg Suc-Ala-Ala-Pro-Phe-pNA is dissolved in 4 ml DMSO (200 mM). This solution is diluted 100 times with the buffer solution described below. The concentration of substrate in the resulting substrate solution is 2 mM.

Inhibitor Solution (0.005 mg/ml):

5 mg trypsin inhibitor type IV-0 (Sigma T-1886) is dissolved in 10 ml water. This solution is dissolved 100 times with the buffer solution described below. The concentration of inhibitor in the resulting inhibitor solution is 0.005 mg/ml.

Enzyme Solution (0.001 mg/ml):

1 mg enzyme is dissolved in 10 ml water. This solution is dissolved 100 times with the buffer solution described below. The concentration of enzyme in the resulting enzyme solution is 0.001 mg/ml.

Buffer Solution (pH 8.6):

15.7 mg Tris is dissolved in an appropriate amount of water and 0.75 ml 30% (w/v) BRIJ (BRIJ 35 polyoxyethylenelaurylether, 30% (w/v), Sigma Cat. No. 430AG-6) is added. The pH is adjusted to 8.6 with 4 M NaOH and the solution is diluted to 1 liter with water.

Assay With Inhibitor 1 volume unit (e.g. 80 µl) inhibitor solution is mixed with 1 volume unit (e.g. 80 µl) enzyme solution in an appropriate reaction vessel (e.g. a spectrophotometer cell or a micro titer plate) and equilibrated at 25° C. for 15 min. 1.375 volume units (e.g. 110 µl) substrate solution is added to the reaction vessel after which the absorbance at 405 nm is followed for 11 min (e.g. by measuring every 10$^{th}$ or 30$^{th}$ second). The slope of the absorbance curve is calculated using linear regression analysis. The slope of the absorbance curve is denoted $\alpha_{inhibitor}$.

Assay Without Inhibitor 1 volume unit (e.g. 80 µl) buffer solution is mixed with 1 volume unit (e.g. 80 µl) enzyme solution in an appropriate reaction vessel (e.g. a spectrophotometer cell or a micro titer plate) and equilibrated at 25° C. for 15 min. 1.375 volume units (e.g. 110 µl) substrate solution is added to the reaction vessel after which the absorbance at 405 nm is followed for 11 min (e.g. by measuring every 10$^{th}$ or 30$^{th}$ second). The slope of the absorbance curve is calculated using linear regression analysis. The slope of the absorbance curve is denoted $\alpha$.

Blank 1 volume unit (e.g. 80 µl) inhibitor solution is mixed with 1 volume unit (e.g. 80 µl) buffer solution in an appropriate reaction vessel (e.g. a spectrophotometer cell or a micro titer plate) and equilibrated at 25° C. for 15 min. 1.375 volume units (e.g. 110 µl) substrate solution is added to the reaction vessel after which the absorbance at 405 nm is followed for 15 min. These measurements are not used in the calculations, but merely serve as a control that no enzyme has been added to the buffer and/or substrate solution.

Calculation of Residual Activity (RA)

The residual enzyme activity (RA) is calculated according to the below formula:

$$RA = (\alpha_{inhibitor}/\alpha) \times 100\%$$

Using the above test, the following results were obtained:

| Enzyme | Residual Activity (%) |
|---|---|
| SAVINASE ® | <5% |
| L217LP + S99SD + S99A | 97.0% |
| S99D + S101R + S103A + V104I + G160S + A194P + V199M + V205I + *216aD | 24.0% |
| S99D + S101R + S103A + V104I + G160S + A194P + V199M + V205I + *216aE | 25.4% |
| S99SD + S99A + S216SDP | 35.0% |
| S99SD + S99A + N155NA | 7.4% |
| S99SD + S99A + N155ND | 10.7% |
| S99SD + S99A + N155NR | 6.5% |
| S99SD + S99A + N155ND | 7.1% |
| L42LN | 69.2% |

What is claimed is:

1. A modified subtilase comprising a mutation in an amino acid sequence of a subtilase, wherein the mutation is an insertion of at least one amino acid residue between:
   (a) positions 51 and 56;
   (b) positions 216 and 217; and/or
   (c) positions 217 and 218;
wherein the positions are numbered according to the amino acid sequence of the mature Subtilisin BPN' of SEQ ID NO: 7 and the modified subtilase has subtilase activity.

2. The modified subtilase of claim 1, which has a residual activity of at least 10% in the Ovo-inhibition assay.

3. The modified subtilase of claim 2, which has a residual activity of at least 15%.

4. The modified subtilase of claim 1, wherein the variant contains two or more insertions.

5. The modified subtilase of claim 4, wherein the variant contains more than two insertions.

6. The modified subtilase of claim 1, wherein the insertion is between positions 51 and 52; positions 52 and 53; positions 53 and 54; positions 54 and 55; or positions 55 and 56.

7. The modified subtilase of claim 6, wherein the insertion is selected from the group consisting of X51XA, X51XT, X51XG, X51XS, X51XD, X51XE, X51XK, X51XR, X51XH, X51XV, X51XC, X51XN, X51XQ, X51XF, X51XI, X51XL, X51XM, X51XP, X51XW and X51XY.

8. The modified subtilase of claim 6, wherein the insertion is selected from the group consisting of X52XA, X52XT, X52XG, X52XS, X52XD, X52XE, X52XK, X52XR, X52XH, X52XV, X52XC, X52XN, X52XQ, X52XF, X52XI, X52XL, X52XM, X52XP, X52XW and X52XY.

9. The modified subtilase of claim 6, wherein the insertion is selected from the group consisting of X53XA, X53XT, X53XG, X53XS, X53XD, XS3XE, X53XK, X53XR, X53XH, X53XV, X53XC, X53XN, X53XQ, X53XF, X53XI, X53XL, X53XM, X53XP, X53XW and X53XY.

10. The modified subtilase of claim 6, wherein the insertion is selected from the group consisting of X54XA, X54XT, X54XG, X54XS, X54XD, X54XE, X54XK, XS4XR, X54XH, X54XV, X54XC, X54XN, X54XQ, X54XF, X54XI, X54XL, X54XM, X54XP, X54XW and X54XY.

11. The modified subtilase of claim 6, wherein the insertion is selected from the group consisting of X55XA, X55XT, X55XG, X55XS, X55XD, X55XE, X55XK, X55XR, X55XH, X55XV, X55XC, X55XN, X55XQ, X55XF, X55XI, X55XL, X55XM, X55XP, X55XW and X55XY.

12. The modified subtilase of claim 1, wherein the insertion is between positions 216 and 217.

13. The modified subtilase of claim 12, wherein the insertion is selected from the group consisting of X216XA, X216XT, X216XG, X216XS, X216XD, X216XE, X216XK, X216XR, X216XH, X216XV, X216XC, X216XN, X216XQ, X216XF, X216XI, X216XL, X216XM, X218XP, X216XW and X216XY.

14. The modified subtilase of claim 1, wherein the insertion is between positions 217 and 218.

15. The modified subtilase of claim 14, wherein the insertion is selected from the group consisting of X217XA, X217XT, X217XG, X217XS, X217XD, X217XE, X217XK, X217XR, X217XH, X217XV, X217XC, X217XN, X217XQ, X217XF, X217XI, X217XL, X217XM, X217XP, X217XW and X217XY.

16. The modified subtilase of claim 1, wherein the subtilase is a sub-group I-S1 subtilase.

17. The modified subtilase of claim 16, wherein the subtilase is selected from the group consisting of subtilisin I168, subtilisin BPN', subtilisin DY, and subtilisin Carlsberg.

18. The modified subtilase of claim 1, wherein the subtilase is a sub-group I-S2 subtilase.

19. The modified subtilase of claim 18, wherein the subtilase is selected from the group consisting of subtilisin 147, subtilisin 309, subtilisin PB92, and subtilisin YaB.

20. The modified subtilase of claim 1, wherein the variant comprises at least one further mutation.

21. The modified subtilase of claim 20, wherein the at least one further mutation is a substitution.

22. The modified subtilase of claim 20, wherein the at least one further mutation is at position 27, 36, 56, 76, 87, 95, 96, 97, 98, 99, 100, 101, 102, 103, 104, 120, 123, 129, 131, 132, 133, 143, 159, 167, 170, 192, 194, 206, 217, 218, 222, 224, 232, 235, 236, 245, 248, 252 or 274.

23. The modified subtilase of claim 22, wherein the variant further comprises the modification S101G+S103A+V104I+G159D+A232V+Q236H+Q245R+N248D+N252K.

24. The modified subtilase of claim 1, further comprising an insertion of at least one additional amino acid residue in the active site loop (b) region from position 95 to 103.

25. A cleaning or detergent composition, comprising the modified subtilase of claim 1 and a surfactant.

26. The composition of claim 25, which additionally comprises an amylase, cellulase, cutinase, lipase, oxidoreductase, another protease, or combination thereof.

27. A method for removal of egg stains from a hard surface or from laundry, comprising contacting the egg stain-containing hard surface or the egg stain-containing laundry with a cleaning or detergent composition of claim 25.

28. An isolated polynucleotide with a DNA sequence encoding a modified subtilase of claim 1.

29. An expression vector comprising the isolated polynucleotide of claim 28.

30. A microbial host cell transformed with the expression vector of claim 29.

31. A microbial host cell of claim 30, which is a bacterium.

32. A method for producing a modified subtilase, comprising
   (a) culturing a host of claim 30 under conditions conducive to the expression and secretion of the modified subtilase, and
   (b) recovering the modified subtilase.

* * * * *